(12) United States Patent
Srivastava et al.

(10) Patent No.: US 7,714,063 B2
(45) Date of Patent: May 11, 2010

(54) SOLID SUPPORT FOR FMOC-SOLID PHASE SYNTHESIS OF PEPTIDES

(75) Inventors: Kripa Shanker Srivastava, Chesterfield, MO (US); Matthew Ryan Davis, St. Louis, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 12/264,948

(22) Filed: Nov. 5, 2008

(65) Prior Publication Data

US 2009/0131587 A1    May 21, 2009

Related U.S. Application Data

(60) Provisional application No. 60/988,148, filed on Nov. 15, 2007.

(51) Int. Cl.
   A61K 47/48     (2006.01)
   A61K 31/405    (2006.01)
   C08G 73/06     (2006.01)
   C08F 6/22      (2006.01)
   C07K 5/00      (2006.01)

(52) U.S. Cl. .................. 525/54.1; 525/55; 528/423; 528/492; 530/333; 514/415

(58) Field of Classification Search ............. 525/54.1, 525/55; 528/423, 492; 530/333; 514/415
   See application file for complete search history.

(56) References Cited

U.S. PATENT DOCUMENTS 4,005,063 A    1/1977    Gendrich et al.

OTHER PUBLICATIONS

Acta Chemica Scandinavica (1995), 49(8), 599-608, Berg et al.*
Gevorkyan, et al., Khimiko-Farmatsevticheskii Zhurnal (1988), 22(190), 1203-7.*
Estep et al., Indole Resin: A Versatile New Support for the Solid-Phase Synthesis of Organic Molecules, J. Org. Chem., 1998, 63, 5300-5301.
Sarantakiss et al., "Solid Phase Synthesis of Sec-Amides and Removal from the Solymeric Suuport Under Mild Condidtions", Tetrahedron Letters, 1997, vol. 38, No. 42, 7325-7328.
Swayze, Eric E., "Secondary Amide-based Linkers for Solid Phase Organic Synthesis", Tetrahedron Letters, 1997, vol. 38, No. 49, 8465-8468.
Bhattacharyya et al., "Expedient synthesis of secondary amines bound to indole resin and cleavage of resin-bount urea, amide and sulfonamide under mild conditions", Tetrahedron Letters, 2003, 44, 6099-6102.
Subramanyam et al., "Solid-phase synthesis of peptidyl x-keto heterocycles", Tetrahedron Letters, 2002, 43, 6313-6315.
Cambell et al., "A Reductive Alkylation Procedure Applicable to Both Solution-and Solid-Phase Syntheses of Secondary Amines", J. Org. Chem., 1996, 61, 6720-6722.
Ramage et al., "Design of a Versatile Linker for Solid Phase Peptide Synthesis: Synthesis of C-Terminal Primary/Secondary Amides and Hydrazides", Tetrahedron Letters, 1993, vol. 34, No. 41, 6599-6602.
Dimare et al., "A Mild, Pyridine-Borane-Based Reductive Amination Protocol", J. Org. Chem., 1995, 60, 5995-5996.
Brown et al., "Alkylation of Rink's Amide Linker on Polystyrene Residn: A Reductive Amination Approach to Modified Amine-Linkers for the Solid Phase Synthesis of N-Substituted Amide Derivatives", Tetrahedron Letters, 1997, vol. 38, No. 49, 8457-8460.
Ellman et al., "Solid-Phase Synthesis of 1,4-Benzodiazepine-2,5-diones. Library Preparation and Demonstration of Synthesis Generality", J. Org. Chem., 1997, 62, 1240-1256.
Merrifield, Robert Bruce, "Solid Phase Synthesis (Nobel Lecture)", Angewandte Chemie, Oct. 1995, vol. 24, No. 10, 799-892.
Kornreich et al., "Peptide N-alkylamides by solid phase synthesis", Int. J. Peptide Protein Res., 1985, 25, 414-420.
Coy et al., "Stimulatory and Inhibitory Analogs of Luteinizing Hormone Releasing Hormone", Agonistic and Antagonistic LH-RH Analogs, Biochemistry, 1974, 13, 323-326.
Coy et al., "Synthesis and Biological Activity of LH-RH Analogs Modified at the carboxyl Terminus", Journal of Medicinal Chemistry, 1975, vol. 18, No. 3, 275-277.
Coy et al., "Analogs of Luteinizing Hormone-Releasing Hormone with Increased Biological Activity Produced by D-Amino Acid Substitutions in Position 6", J. Med. Chem., 1976, 19(3), 423-425.
EMD BioSciences Catalogue 2004-2005, "Indole resins", 244.
Zompra et al., "Looking for an Api Peptide?", Chemistry Today, 24(4), 49-51.
Poh et al., "Complexation of Polyaromatic Hydrocarbons with disodium 1,8-Disulfonato-3,4,5,6-Acridinetetracarboxylic Acid in Water", Tetrahedron Letters, 1996, vol. 37, No. 46, 8451-8454.

* cited by examiner

*Primary Examiner*—Ling-Siu Choi
*Assistant Examiner*—Sonya Wright

(57) ABSTRACT

The present invention provides compositions and processes for the solid phase synthesis of polypeptides. In particular, the present invention provides solid supports and processes for preparing solid supports for the synthesis of polypeptides.

20 Claims, No Drawings

SOLID SUPPORT FOR FMOC-SOLID PHASE SYNTHESIS OF PEPTIDES

CROSS REFERENCE TO RELATED APPLICATIONS

This application claims the priority of U.S. provisional application No. 60/988,148, filed Nov. 15, 2007, which is hereby incorporated by reference in its entirety.

FIELD OF THE INVENTION

The present invention generally relates to compositions and processes for the solid phase synthesis of polypeptides. In particular, the present invention provides solid supports and processes for preparing solid supports for the synthesis of polypeptides.

BACKGROUND OF THE INVENTION

Polypeptide synthesis may be either solid-phase peptide synthesis (SPPS) or solution-phase synthesis. Unlike ribosome protein synthesis, solid-phase protein synthesis generally proceeds from the C-terminus to N-terminus. There are several groups of peptides and peptidomimetic compounds characterized by derivatization at the C-terminus of the peptide chain. One of these groups includes peptides having C-terminus secondary amides. Within the category of peptides having C-terminus secondary amides, one of the most important families of pharmaceutical products is GnRH agonist analogues as well as antagonists. This family consists of various peptides such as Leuprolide, Deslorelin, Buserelin, Alarelin, Fertirelin, Histrelin, and other analogues.

Peptides with C-terminus secondary amides have traditionally been prepared by SPPS using Boc/Benzyl chemistry either directly on alkylated amino methyl resin (J. Rivier, et al, IJPPR (1985) 25:414-420) or indirectly on Merrifield resin followed by aminolysis where the C-terminus amino acid of the peptide is attached to the solid support by an ester bond (D. H. Coy et al., Biochemistry (1974) 13:303). Both the direct method and indirect method, however, are plagued with drawbacks. With the direct method, peptide yield is relatively low after acidolysis. The indirect method, in addition to slow reaction times, also can suffer from racemization, is cumbersome, and cannot be used with peptides containing protected glutamic acid and/or aspartic acid because their benzyl esters will also undergo aminolysis. Moreover, Boc-SPPS generally utilizes environmentally unfriendly reagents, such as hydrogen fluoride (HF).

To overcome the problems associated with Boc-SPPS synthesis of peptides, Fmoc-SPPS has gained in popularity because of its use of environmentally safer reagents and comparatively milder reaction conditions. In particular, Fmoc-SPPS peptide synthesis avoids the use of HF. One resin that can be utilized for the Fmoc-SPPS synthesis of peptides with secondary amides is a resin bound amine (A. A. Zompra, et al., Chemistry Today (2006) 24(4):49-51). This resin has also been successfully used for the synthesis of small organic molecules such as secondary amides, ureas, sulfonamides, and guanidines (K. G. Estep, et al., J. Org. Chem. (1998) 63:5300-5301). Amine bound resins, however, have several drawbacks for Fmoc-SPPS synthesis of peptides. For example, the synthesis of secondary amides has been reported to be difficult, while the synthesis of sulfonamides has been reported to be unsuccessful. These supports also require expensive intermediates, multi-step reactions, and/or longer reaction time. Taken together, currently available amine bound supports are generally not practical or economical for the large-scale production of peptides with secondary amides. A need therefore exists for a solid support that is economical to produce, and that can be used for Fmoc-SPPS synthesis of polypeptides in high purity and yield, and in particular, for the synthesis of peptides with C-terminus secondary amides.

SUMMARY OF THE INVENTION

Among the various aspects of the present invention is the provision of a solid support for the synthesis of peptides. The solid support is a compound comprising Formula (I):

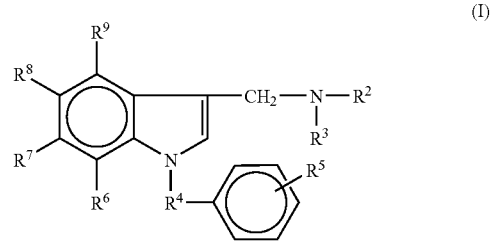

wherein:
$R^2$ and $R^4$ are hydrocarbyl;
$R^3$ is selected from the group consisting of hydrogen, a protecting group, an amino acid residue, and a peptide;
$R^5$ is a solid support comprising at least one polymer; and
$R^6$, $R^7$, $R^8$, and $R^9$ are independently selected from the group consisting of hydrogen, hydrocarbyl, and substituted hydrocarbyl.

Another aspect of the invention encompasses a process for making a solid support for the synthesis of polypeptides. The process comprises a first step in which a compound comprising formula (1) is combined with a compound comprising formula (2) in the presence of a base to produce a compound comprising formula (3). The compound comprising formula (1) has the following structure:

wherein:
$R^4$ is hydrocarbyl; and
$R^5$ is a solid support comprising at least one polymer.

The compound comprising formula (2) has the following structure:

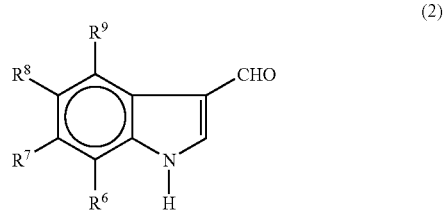

wherein:
$R^6$, $R^7$, $R^8$, and $R^9$ are independently selected from the group consisting of hydrogen, hydrocarbyl, and substituted hydrocarbyl.

The compound comprising formula (3) has the following structure:

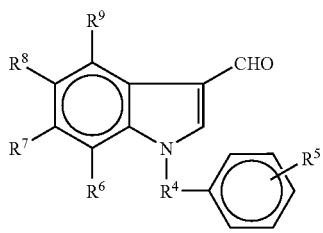

(3)

wherein:
$R^4$ is hydrocarbyl;
$R^5$ is a solid support comprising at least one polymer; and
$R^6$, $R^7$, $R^8$, and $R^9$ are independently selected from the group consisting of hydrogen, hydrocarbyl, and substituted hydrocarbyl.

The process further comprises a second step in which the compound comprising formula (3) is contacted with a reducing agent and a compound comprising $R^2NH_2$, wherein $R^2$ is hydrocarbyl, to produce a solid support comprising formula (I):

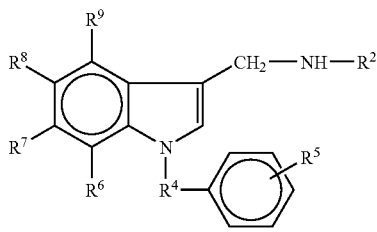

(I)

wherein:
$R^2$ and $R^4$ are hydrocarbyl;
$R^5$ is a solid support comprising at least one polymer; and
$R^6$, $R^7$, $R^8$, and $R^9$ are independently selected from the group consisting of hydrogen, hydrocarbyl, and substituted hydrocarbyl.

A further aspect of the invention provides a method for synthesizing a polypeptide. The process comprises a first step in which the carboxyl group of an amino acid is activated, wherein the amino acid has its amine protected by a Fmoc group and its side chain protected by an acid labile group. The second step comprises coupling the activated amino acid to the amino group of a solid support comprising Formula (I):

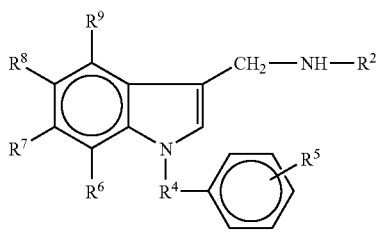

(I)

wherein:
$R^2$ and $R^4$ are hydrocarbyl;
$R^5$ is a solid support comprising at least one polymer; and
$R^6$, $R^7$, $R^8$, and $R^9$ are independently selected from the group consisting of hydrogen, hydrocarbyl, and substituted hydrocarbyl.

The process further comprises a third step in which the solid support is treated with a base to deprotect the amine group of the amino acid protected with Fmoc, and a final step in which steps 1-3 are repeated until the target polypeptide is synthesized.

Other aspects and features of the invention are described in more detail below.

DETAILED DESCRIPTION OF THE INVENTION

A solid support has been discovered that can be utilized to produce peptides using Fmoc-SPPS. In particular, the solid support can be utilized to produce peptides having C-terminus secondary amides in both high yield and purity. The invention also encompasses a process to make the solid support in an economical manner using a two-step reaction scheme. Advantageously, as illustrated in the Examples, the solid support allows the direct release of the final peptide-alkylamide after treatment with a mild acid. By varying the concentration of the mild acid, either a fully or partially protected peptide secondary amide may be also released from the solid support.

(I) Solid Support

The solid support of the invention generally comprises a polymeric resin covalently conjugated to a linker. In one embodiment, the solid support is a compound comprising Formula (I):

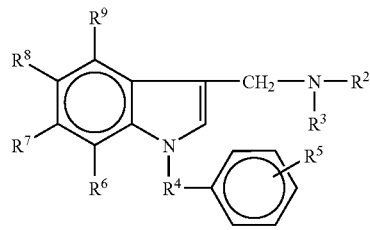

(I)

wherein:
$R^2$ and $R^4$ are hydrocarbyl;
$R^3$ is selected from the group consisting of hydrogen, a protecting group, an amino acid residue, and a peptide;
$R^5$ is a solid support comprising at least one polymer. In an exemplary embodiment, $R^5$ is at the para position from $R^4$; and
$R^6$, $R^7$, $R^8$, and $R^9$ are independently selected from the group consisting of hydrogen, hydrocarbyl, and substituted hydrocarbyl.

In one embodiment for compounds comprising Formula (I), $R^2$ and $R^4$ are alkyl groups having from 1 to 8 carbon atoms; $R^3$ is Fmoc; and $R^6$, $R^7$, $R^8$, and $R^9$ are hydrogen.

In yet another embodiment for compounds comprising Formula (I), $R^2$ and $R^4$ are alkyl groups having from 1 to 8 carbon atoms; $R^3$ is an amino acid; and $R^6$, $R^7$, $R^8$, and $R^9$ are hydrogen. The amino acid may be protected (i.e., by a protecting group as described in section III) or unprotected.

In an additional embodiment for compounds comprising Formula (I), $R^2$ and $R^4$ are alkyl groups having from 1 to 8 carbon atoms; $R^3$ is a peptide; and $R^6$, $R^7$, $R^8$, and $R^9$ are hydrogen. The peptide may be protected or unprotected. In one alternative of this embodiment, the peptide has a C-terminus secondary amine. In yet another alternative of this embodiment, the peptide is a GnRH agonist analogue or antagonist. Examples of suitable GnRH agonist analogues include Leuprolide, Deslorelin, Buserelin, Alarelin, Fertirelin, Histrelin, and other analogues.

In an additional embodiment, the solid support having Formula (I) is a compound comprising the following structure:

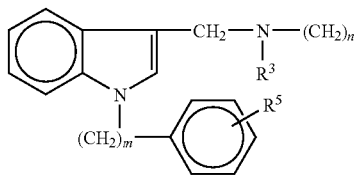

wherein:
R³ and R⁵ are as described above;
m is an integer from 1 to 8; and
n is an integer from 1 to 8.

In an exemplary embodiment, the solid support having Formula (I) is a compound comprising the following structure:

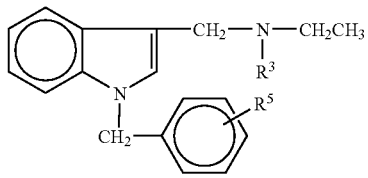

wherein R³ and R⁵ are as described above.

For each of the foregoing embodiments, R⁵, the solid support, may be comprised of one or more suitable polymeric materials comprising phenyl groups in the backbone. Suitable solid supports include, but are not limited to, polyacrylamide, polystyrene, polyacrylate, hydroxethylmethacrylate, polyamide, polyethylene, polyethyleneoxy, or copolymers and grafts of such. In an exemplary embodiment, the material is a synthetic polymer of styrene. To increase the stability and insolubility in organic solvents, typically the polystyrene resin will be cross-linked using from about 0.5% to about 2% divinylbenzene. While the size and shape of the resin can and will vary, typically the resin will have a spherical shape and display a broad particle size distribution in the range of about 20 μm to about 150 μm. Stated another way, the size may range from about 100 mesh to about 400 mesh.

(II) Process for Making the Solid Support

The solid support comprising Formula (I) may be made via a two-step reaction scheme. With reference to the reaction schemes illustrated below and in the examples, in the first step, a linker moiety comprising an aldehyde group (compound 2) is covalently conjugated to a polymeric material containing a chlorine hydrocarbyl group (compound 1) to produce a compound comprising Formula 3. In the second step, compound 3 is derivatized with a hydrocarbyl amide group by reductive amination to produce a solid support of the invention comprising Formula (I). The compound comprising Formula (I) may be further reacted with the protecting group Fmoc to produce the compound comprising Formula 4, as illustrated in the examples.

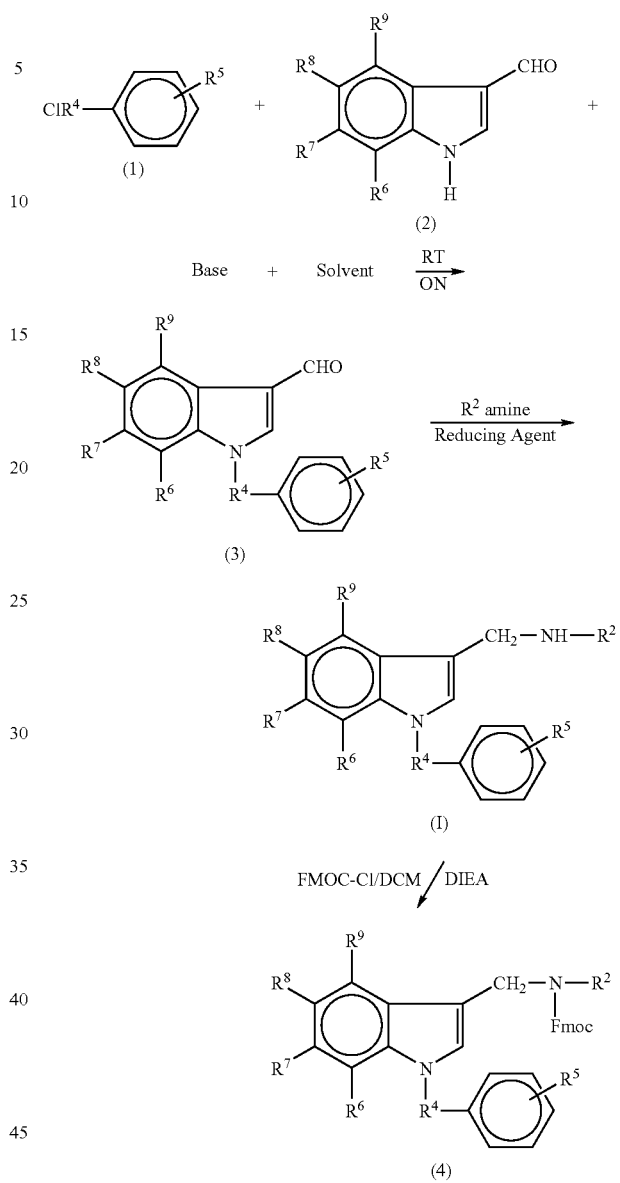

wherein:
R², R³, R⁴, R⁵, R⁶, R⁷, R⁸, and R⁹ are as described in section (I) for compounds comprising Formula (I).

In another iteration, the process of the invention utilizes the following reactants:

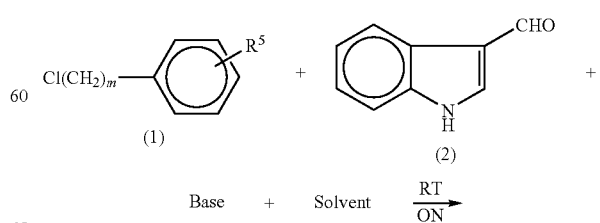

-continued

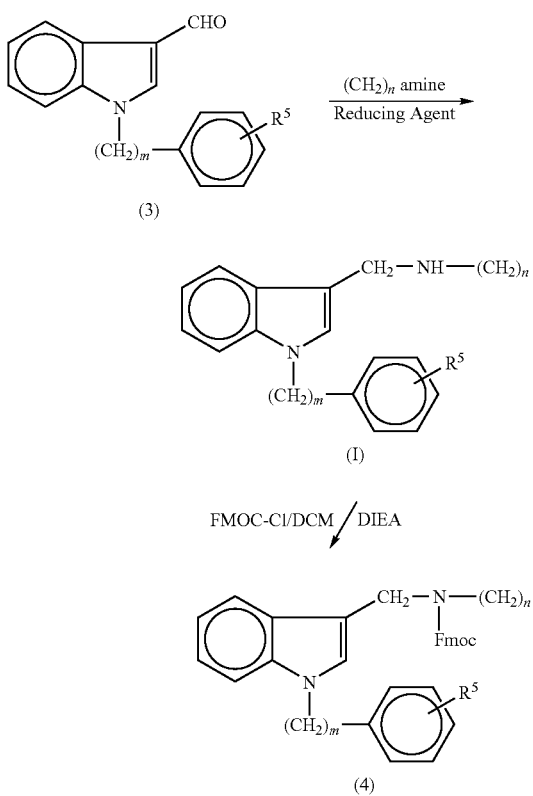

wherein:
R⁵ is as described in section (I) for compounds comprising Formula (I); and
m and n are independently integers from 1 to 8.

In an exemplary embodiment, the process of the invention utilizes the reactants detailed in the examples.

The selection of the specific base and solvent utilized in step 1 of the process can and will vary depending upon the other reactants. Typically, the base will be sodium methoxide. Alternatively, the base may be a carbonate base or anhydrous potassium. Non-limiting examples of suitable carbonate bases include potassium carbonate, lithium carbonate, sodium carbonate, magnesium carbonate, calcium carbonate, and strontium carbonate. In a preferred embodiment, the base may be potassium carbonate. Suitable solvents generally include aprotic solvents such as dimethylformamide, dimethyl sulfoxide, acetonitrile, methanol, ethanol, tetrahydrofuran, and 1,4-dioxane.

The reducing agent used for reductive amination in step 2 of the process also can and will vary. For example suitable reducing agents include tetramethylamine triacetoxyborohydride, boron/pyridine, sodium borohydride, sodium cyanoborohydride, diisobutylaluminium hydride, lithium aluminium hydride, and titanium isopropoxide sodium borohydride. In an exemplary embodiment, the reducing agent is sodium borohydride. Solvents that may be used in combination with the reducing agent include aprotic solvents, protic solvents or a combination thereof. Suitable aprotic solvents include dimethylformamide, dimethyl sulfoxide, trimethyl orthoformate, dichloromethane, dichloroethane, tetrahydrofuran, and 1,4-dioxane. Non-limiting examples of protic solvents include ethyl alcohol, n-propanol, n-butanol, acetic acid, isopropanol, methanol, and formic acid.

As will be appreciated by a skilled artisan, the amount of various reactants used in the process can and will vary without departing from the scope of the invention. In the first step of the process, generally speaking, the amount of compound 1 to the amount of compound 2 to the amount of base may be expressed as a molar ratio of from about 1:1:1 to about 1:5:5. In one exemplary embodiment, the amount of compound 1 to the amount of compound 2 to the amount of base is a molar ratio of about 1:1.5:1.5. In the second step of the process, the amount of compound 3 to the amount of hydrocarbyl amine to the amount of base may be expressed as a molar ratio from about 1:1:1 to about 1:10:20. In one exemplary embodiment, the amount of compound 3 to the amount of hydrocarbyl amine to the amount of base may be expressed as a molar ratio from about 1:2:2 to about 1:5:10.

The reaction conditions for steps 1 and 2 of the process, such as reaction time, temperature, and pH may also vary without departing from the scope of the invention. For step 1 of the process, by way of non-limiting example, the reaction time may range from several hours to several days, the reaction temperature may range from approximately room temperature to about 100° C., and the reaction is generally conducted at an approximately basic pH. For step 2 of the process, by way of further non-limiting example, the reaction time may range from about several hours to several days, the reaction temperature is from approximately room temperature to about 100° C., and the reaction is generally conducted at an approximately basic pH. Exemplary reaction parameters for both step 1 and step 2 of the process are detailed in the examples.

(III) Use of the Solid Support to Synthesize Peptides

The solid support comprising Formula (I) may be utilized to synthesize peptides via Fmoc chemistry. In general, the method involves the use of the base labile Fmoc-amino protecting groups on the initial amino acid covalently coupled to the solid support and on each amino acid that is sequentially added to the growing peptide chain on the solid support. After each coupling step the terminal Fmoc amino acid protecting group is then cleaved by base treatment to provide a free amine group ready for coupling in the next addition cycle. Acid-labile protecting groups generally protect the amino acid side chains. In this context, Fmoc chemistry is based on the orthogonal concept in the sense that the two protecting groups belong to independent classes (i.e., Fmoc is base labile and side chain protecting groups are acid labile) and can be removed by different mechanisms. The two groups can be removed, therefore, in any order in the presence of the other group.

Accordingly, with reference to the diagram below, the synthesis of peptides by Fmoc-SPPS using the solid support of the invention involves the following general steps: (1) base deprotection of the solid support (I) with Fmoc protecting group; (2) activation of an incoming amino acid that has its side chain protected by an acid labile group; (3) coupling the amino acid to the growing polypeptide under basic pH; (4) repeating steps (1) to (3) until the desired polypeptide is synthesized; (5) Fmoc deprotection; (6) cleavage of the peptide from the support to yield the desired peptide-alkylamide.

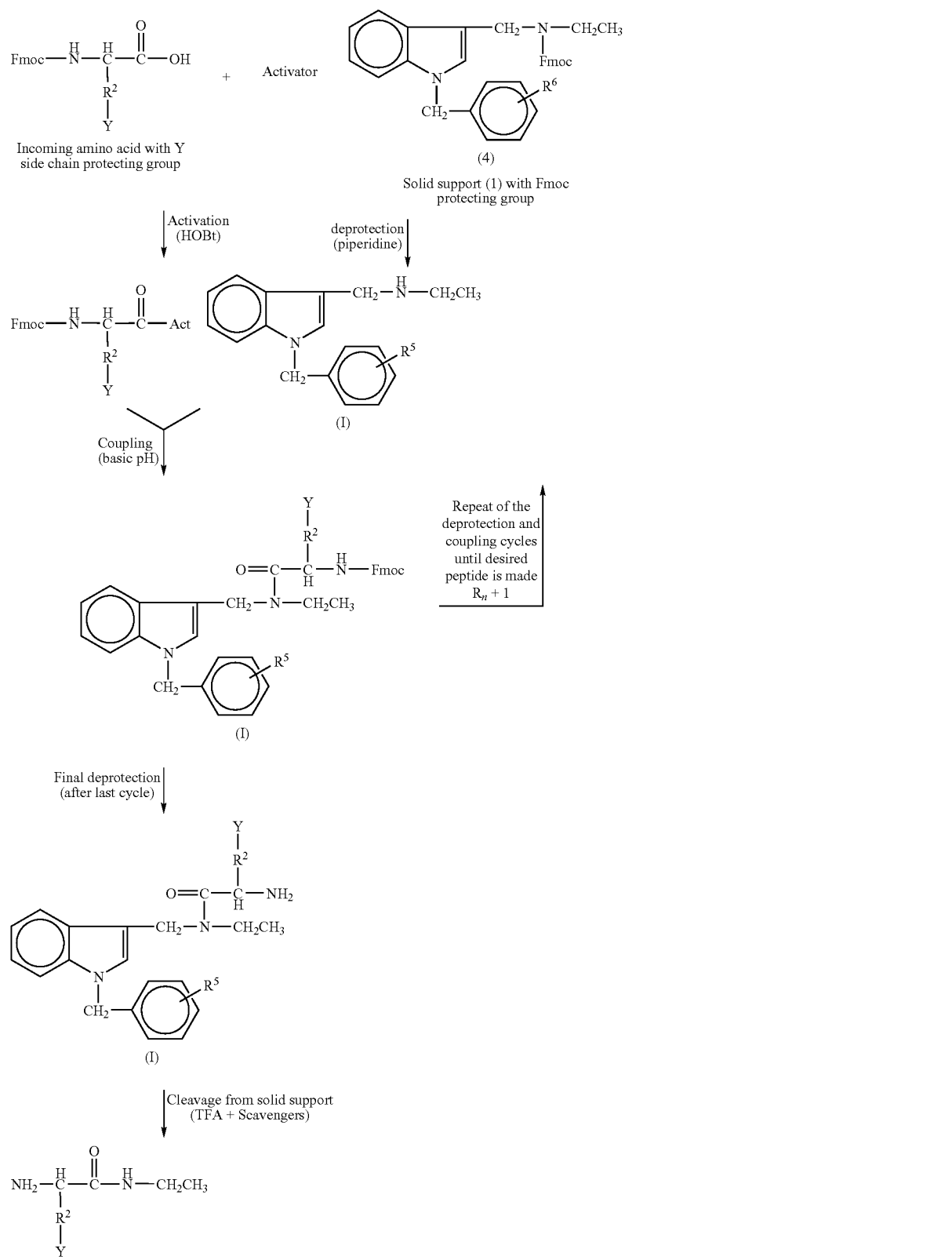
Amine groups protected with Fmoc may be deprotected by treatment with an organic base. Suitable organic bases include piperidine, cyclohexylamine, 1,5-diazabicyclo[5,4,0]undec-5-ene, ethanolamine, pyrrolidine 1,8-diazabicyclo

[5.4.0]undec-7-ene, diethylamine, morpholine, and mixtures thereof. In an exemplary embodiment, the base is piperidine. Typically, the amount of organic base used in Fmoc deprotection when the base is piperidine will range from about 5% to about 50% (v/v).

The Fmoc deprotection reaction is carried out in the presence of a solvent at approximately room temperature. Non-limiting examples of suitable solvents include anisole, dimethylformamide, dimethylsulfoxide, dimethyl acetamide, dichloromethane, N-methylpyrrolidinone, and mixtures thereof. A list of additional suitable solvents can be found in Tetrahedron Letters 39:8451-54 (1998), which is incorporated herein by reference in its entirety.

Each incoming amino acid that is added to the growing peptide chain is generally protected with an acid-labile side-chain protecting group. The acid-labile protecting groups used are typically based on butyl and trityl groups. For example, the group may be a tert-butyl moiety, such as, tert-butyl ethers for Ser, and Thr, tert-butyl esters for Asp, Glu, 2-Cl-trityl for Tyr, and Boc for Lys, His. Several suitable Fmoc-amino acids derivatives are commercially available.

As depicted in the diagram above, for the coupling reaction the carboxyl group of the incoming amino acid is usually activated. Suitable activating compounds include those belonging to the aromatic oximes class. In an exemplary embodiment, the aromatic oxime is selected from 1-hydroxy-benzotriazole (HOBt), and 1-hydroxy-7-aza-benzotriazole (HOAt). Other suitable activating compounds include HATU/HOAT, PyBOP/HOBT, or OPFP preactivated amino acids/HOBT.

The amount of the various reactants in the coupling reaction can and will vary greatly. Typically the amount of solid support to the amount of Fmoc-amino acid to the amount of activating compound will be a molar ratio ranging from about 1:1:1 to 1:5:5. In one embodiment, the amount of solid support to the amount of Fmoc-amino acid to the amount of activating compound is a molar ratio of about 1:1.5:1.5.

The progress of amino acid couplings can be followed using ninhydrin, or p-chloranil test, as described in the examples. The ninhydrin solution turns dark blue (positive result) in the presence of a free primary amine but is otherwise colorless (negative result). The p-chloranil solution will turn the solution dark black or blue in the presence of a primary amine if acetaldehyde is used as the solvent or in the presence of a secondary amine, if acetone is used instead; the solution remain colorless or pale yellow otherwise.

Once the final amino acid has been added, the polypeptide may be cleaved from the solid support with a mild acid in the presence of appropriate scavengers to yield a peptide-alkylamide. In general, the solid support will be treated with trifluoroacetic acid (TFA) in the presence of appropriate scavengers. The choice of scavengers is dependent on the amino acid sequence of the peptide. These scavengers include phenol, water, 1,2-ethanedithiol, and triisopropylsilane. In certain embodiments it may be desirable to deprotect all of the amino acids, or selectively deprotect certain amino acids, or to deprotect the amino acids while leaving the peptide covalently conjugated to the solid support. By varying the concentration of the mild acid, either a fully or partially protected peptide secondary amide may be released from the solid support. The amount of TFA typically used for cleavage of the protected peptide from the solid support may range from about 1% to about 10% (v/v). More typically the amount of TFA used for cleavage of the protected peptide from the solid support may range from about 3% to about 5% (v/v).

The peptide is typically analyzed by chromatography, such as reverse phase HPLC or mass spectrometry after it is cleaved from the solid support. As will be appreciated by a skilled artisan the yield and purity can and will vary depending upon the peptide produced. The yield will generally range from about 40% to greater than about 90%. More typically, the yield will range from about 60% to greater than about 80%. The purity will generally range from about 65% to greater than about 99% as determined by HPLC.

While it is envisioned that the solid support may be utilized to synthesize any peptide of interest, in an exemplary embodiment the peptide may have a C-terminus secondary amine. An example of a class of peptides having C-terminus secondary amines is the class of GnRH agonist analogues or antagonists. Examples of GnRH agonist analogues include Leuprolide, Deslorelin, Buserelin, Alarelin, Fertirelin, Histrelin, and other analogues. In an exemplary embodiment, the peptide is Leuprolide having the following amino acid sequence pGlu-His-Trp-Ser-Tyr-D-Leu-Leu-Arg-Pro-NHEt (SEQ. ID NO:1). The examples illustrate synthesis of Leuprolide, Buserelin, Deslorelin, and Alarelin using the solid support of the invention.

DEFINITIONS

"AcOH" as used herein stands for acetic acid.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "base" is intended to mean an organic or inorganic substance with a pKa of greater than about 8.

"Boc" as used herein stands for tert-butyloxycarbonyl.

"DIC" as used herein stands for diisopropylcarbodiimide.

"DIEA" as used herein stands for diisopropylethylamine.

"DCM" as used herein stands for dichloromethane.

"DMF" as used herein stands for dimethylformamide.

"EAM-IA-AMR" as used herein stands for 3-ethylaminomethyl-indoylacetyl-amino methyl resin.

"EAM-IMR" is an embodiment of the solid support of the invention comprising Formula (I). It is also referred to by its chemical name 3-ethylaminomethyl-indolymethyl resin.

"EDT" as used herein stands for ethanedithiol.

"EtNH$_2$" as used herein stands for ethylamine.

"EtOH" as used herein stands for ethanol or ethyl alcohol.

"Fmoc" as used herein stands for 9-fluorenyl-methoxycarbonyl.

The terms "halogen" or "halo" as used herein alone or as part of another group refer to chlorine, bromine, fluorine, and iodine.

The terms "hydrocarbon" and "hydrocarbyl" as used herein describe organic compounds or radicals consisting exclusively of the elements carbon and hydrogen. These moieties include alkyl, alkenyl, and alkynyl moieties. These moieties also include alkyl, alkenyl, and alkynyl moieties substituted with other aliphatic or cyclic hydrocarbon groups, such as alkaryl, alkenaryl and alkynaryl. Unless otherwise indicated, these moieties preferably comprise 1 to 20 carbon atoms.

"HOBT" as used herein stands for 1-hydroxybenzotriazole.

"I-CHO" as used herein stands for indole-3-carboxyaldehyde.

"IMR-CHO" as used herein stands for 3-formyl-indolyl methyl resin or 3-formyl-indolyl Merrifield resin.

"$K_2CO_3$" as used herein stands for potassium carbonate.

"MeOH" as used herein stands for methanol or methyl alcohol.

"$NaBH_3CN$" or "$NaCNBH_3$" as used herein stands for sodium cyanoborohydride.

"$NaBH_4$" as used herein stands for sodium borohydride.

"NaOH" as used herein stands for sodium hydroxide.

"ON" as used herein stands for overnight.

"RCM" as used herein stands for Merrifield resin or chloromethyl resin.

"RT" as used herein stands for room temperature.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

"THF" as used herein stands for tetrahydrofuran.

"TFA" as used herein stands for trifluoroacetic acid.

"$Ti(O^iPr)_4$" as used herein stands for titanium isopropoxide.

"TIS" as used herein stands for triisopropylsilane.

"TMOF" as used herein stands for trimethylorthoformate or methylorthoformate.

As various changes could be made in the above compounds, products and methods without departing from the scope of the invention, it is intended that all matter contained in the above description and in the examples given below, shall be interpreted as illustrative and not in a limiting sense.

EXAMPLES

The following examples detail the synthesis and use of the ethylaminomethyl-indolyl methyl resin (EAM-IMR). Example 1 describes the synthesis of the resin, and Examples 2-5 detail the synthesis of Leuprolide, Buserelin, Deslorelin, and Alarelin, respectively, using the EAM-IMR resin. The general synthesis scheme for the EAM-IMR resin is shown below.

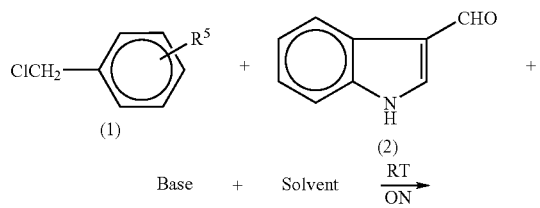

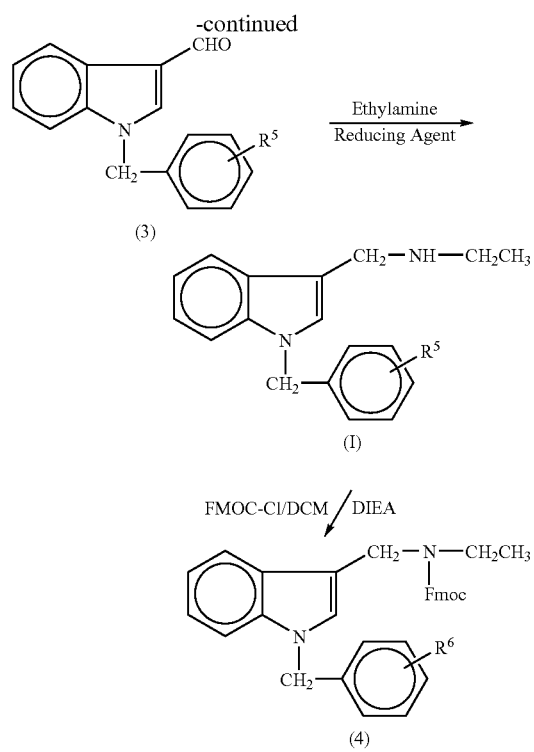

Example 1

Synthesis of 3-Formyl-Indolylmethyl Resin

Step 1

The first step in the synthesis of the resin was to synthesize 3-formyl-indolylmethyl resin (compound 3 in the scheme). Three different methods (A-C) were tried in which the base and the reaction conditions were varied.

Method A: Use of anhydrous $K_2CO_3$ as the base and overnight a Station at room temperature. A mixture of Merrifield resin (6 g, sub.=1.36 mmole/g; total sub.=8.16 mmole or 0.0082 mole), indole-3-carboxaldehyde (1.77 g, 0.0123 mole, 1.5 mole eq.), anhydrous potassium carbonate ($K_2CO_3$; 1.70 g, 0.0123 mole, 1.5 eq.), and 60 ml of dimethylformamide (DMF; 10 ml/g) was stirred in a 250 ml reactor at room temperature overnight (RT/ON) (approximately 20-22 hours). Approximately 50 ml of water was added, the mixture was stirred for 30 minutes and then drained. The resin was washed with water (3×50 ml), 50% DMF-$H_2O$ (2×50 ml), DMF (2×50 ml), dichloromethane (DCM; 2×50 ml), and methanol (MeOH; 2×50 ml), and then dried. The dried resin was colorless and weighed 6.74 g (93.87%), as compared to a theoretical yield of 7.18 g. The net gain in weight was 0.74 g and the percent increase in weight was 12.33%. Nitrogen analysis revealed that the substitution of the aldehyde group was 0.972 mmole/g.

Method B. Use of anhydrous $K_2CO_3$ as the base and RT/ON reaction followed by 60-70° C. for 3 hours. A mixture of 12 g of Merrifield resin (sub.=1.25 mmole/g, total sub.=15 mmole or 0.015 mole), 3.26 g of indole-3-carboxaldehyde (0.0225 mole, 1.5 eq.), 3.11 g of anhydrous potassium carbonate (0.0225 mole, 1.5 eq.), and 120 ml of DMF (10 ml/g) was stirred mechanically in a 1 liter, 3-necked round bottomed (RB) flask at RT/ON. The mixture remained colorless. The mixture then was stirred at 60-70° C. for 3 hours, during which it became brown-colored. After the mixture cooled to room temperature, approximately 120 ml of water was added, and the mixture was stirred for approximately 30 minutes. The mixture was filtered and washed with water (3×120 ml), 50% DMF-$H_2O$ (3×120 ml), DMF (2×100 ml), DCM (2×100 ml), MeOH (2×100 ml), and then dried. The aldehyde resin was off-white colored. The resin weighed 13.72 g (96.9%), whereas the theoretical yield was 14.16 g. The net gain in weight was 1.72 g, and the percent increase in weight was 14.33%. According to N2 analysis, the substitution of the aldehyde group was 1.214 mmole/g.

The experiment was repeated on a 0.025 mole scale using 20.32 g of Merrifield resin (sub.=1.23 mmole/g) as described above. The weight of aldehyde resin was 22.87 g (99.26%), as compared to a theoretical yield of 23.04 g. The net gain in weight was 2.55 g and the percent increase in weight was 12.55%.

Method C. Use of Sodium Methoxide as the base and overnight reaction at 60-70° C. Twelve g of Merrifield resin (sub.=1.36 mmole/g, total sub.=16.32 mmole or 0.01632 mole) was mixed with 3.55 g of indole-3-carboxaldehyde (0.0245 mole, 1.5 eq.) and 120 ml of DMF (10 ml/g). The mixture was mechanically stirred in a 1 liter, 3-necked RB flask under a stream of nitrogen gas. After 1 hour of stirring, sodium methoxide/MeOH solution (0.56 g of Na=0.0245 mole in 15 ml of methanol) was added and the colorless mixture turned into a pink-colored mixture. It was then stirred at 60-70° C. overnight (approximately 20 hours) under a nitrogen stream. After it cooled to room temperature, it was filtered and washed with DMF (1 time), MeOH (1 time), water (3 times), MeOH (2 times), DCM (2 times), and MeOH (2 times), using approximately 100-120 ml of solvent each time. It was dried overnight; the resin was a light cream-color and weighed 13.4 g (93.38%), as compared to a theoretical yield of 14.35 g. The net gain in weight was 1.4 g and the percent increase in weight was 11.7%. Nitrogen analysis revealed that the substitution of the aldehyde group was 1.178 mmole/g.

Method B was selected as the process of choice for synthesizing 3-formyl-indolylmethyl resin. Method B utilized $K_2CO_3$ as the base and the reaction comprised two steps, i.e., room temperature for about 20 hours and 60-70° C. for 3 hours.

Step 2

In the second step of the process, the EAM-IMR resin (compound I in the scheme) was prepared via ethylamine loading by reductive amination. Five different synthesis methods (A-E) were tested.

Method A. Reduction with $NaBH_4$ in THF+EtOH 4:1) (1). Two g of 3-aldehyde-indolylmethyl resin (IMR-CHO) (sub.=1.2 mmole/g; total sub.=2.4 mmole or 0.0024 mole) was swelled in 20 ml of tetrahydrofuran (THF) by stirring for approximately 10 minutes. The resin was filtered and then mixed with 40 ml of THF, 0.8 ml ethylamine (12 mmole, 5 eq.) was added, and the mixture was stirred overnight (approximately 20 hours). $NaBH_4$ (0.91 g, 24 mmole, 10 eq.) and EtOH (10 ml) were added and the mixture was stirred for 6-7 hours. Approximately 20 ml of water was added, the mixture was stirred for 10-15 minutes, and then filtered. The resin was washed with water, MeOH, DMF, and MeOH (2-3 times each), and then dried. The ethylamine loaded resin was colorless and weighed 2.11 g. A sample (100 mg) of the ethylamine loaded resin was reacted with Fmoc-Cl in DCM containing 10% diisopropylethylamine (DIEA) for 2-3 hours. It was filtered and washed with DCM, DMF, DCM, and MeOH, and then dried to yield the Fmoc-EAM-IMR. Substitution was found to be 0.79 mmole/g (using the DBU method). It was reacted again with Fmoc-Cl to reconfirm the reaction. Substitution was found to be 0.85 mmole/g (DBU method).

Method B. Reduction with $NaBH_4$ in DMF+EtOH (3:1) (4:1). Three g of IMR-CHO (sub.=0.972 mmole/g, total sub.=3 mmole) was stirred with approximately 30 ml of DMF for approximately 30 minutes. After draining the resin, it was mixed with 24 ml of DMF+EtOH (3:1), 1 ml ethylamine (15 mmole, 5 eq.), and trimethylorthoformate (TMOF; 0.7 ml, 6 mmole, 2 eq.) were added, and the mixture was stirred ON (approximately 18 hours). $NaBH_4$ (1.2 g, 30 mmole, 10 eq.) and 30 ml of EtOH+MeOH (1:1) were added and the mixture was stirred for approximately 6.5 hours. It was filtered, washed with DMF (1 time), $H_2O$ (2 times), 60% DMF-$H_2O$ (2 times), DMF (2 times), and MeOH (3 times), and then dried. The resin was colorless and weighed 2.98 g. A sample of it (150 mg) was reacted with Fmoc-Cl in DCM containing 10% DIEA to generate Fmoc-EAM-IMR. Substitution was 0.90 mmole/g (DBU method).

The experiment was repeated with 3 g of IMR-CHO in 30 ml of DMF+EtOH (4:1), without using TMOF. The yield of ethylamine loaded resin was 2.88 g. A sample of it (150 mg) was converted into Fmoc-EAM-IMR using Fmoc-Cl. Substitution was 0.57 mmole/g (DBU method).

The experiment was repeated again using 22.8 g of IMR-CHO (sub.=1.21 mmole/g, 27.6 mmole/total) in 125 ml of DMF+EtOH (4:1), 9 ml of ethylamine (0.138 mole, 5 eq.), 3 ml of TMOF (27.66 mmole, 1 eq.) and 10.5 g of $NaBH_4$ (0.276 mole, 10 eq.) as described above to yield 22.86 g of EAM-IMR. A sample of it (150 mg) was converted into Fmoc-EAM-IMR using Fmoc-Cl. Substitution was 0.48 mmole/g (DBU method).

Method C. Reduction with $NaCNBH_3$ in THF+TMOF (1:1) (2). IMR-CHO (4 g, sub.=1.2 mmole/g, total sub=4.8 mmole) was swelled in 50 ml DMF for approximately 2 hours and drained. The resin was mixed with 52 ml of THF+TMOF (1:1), 0.8 ml of ethylamine (12 mmole=0.012 mole, 2.5 eq.) was added and the mixture was stirred for 4-5 hours. Twelve ml of 1 M $NaCNBH_3$/THF (12 mmole, 2.5 eq.) and 0.96 ml of acetic acid (16.8 mmole, 3.5 eq.) were added and the mixture was stirred for 2-3 hours. The resin was filtered and washed with THF (1 time), 50% THF—$H_2O$ (2 times), DMF (1 time), MeOH (2 times), DCM (2 times), and MeOH (2 times). It was dried it to get a light pink colored resin that weighed 4.17 g. A sample of it (150 mg) was reacted with Fmoc-Cl to get Fmoc-EAM-IMR. Substitution was 0.49 mmole/g (DBU method).

Method D. Reduction with $NaCNBH_3$ in TMOF+MeOH (2:1) (3). Three g of IMR-CHO (sub.=0.972 mmole/g, 3 mmole/total) was stirred in 30 ml of DMF for 30 minutes and then drained. It was mixed with 24 ml of TMOF+MeOH (2:1), 1 ml of ethylamine (15 mmole, 5 eq.) was added, and the mixture was stirred overnight (approximately 16 hours). Two g of $NaCNBH_3$ (30 mmole, 10 eq.) and 20 ml of MeOH were added, and the mixture was stirred for 6-7 hours. The resin was filtered, washed with THF (1 time), $H_2O$ (2 times), 50% DMF-$H_2O$ (2 times), DMF (2 times), and MeOH (3 times). The resin was dried; it was light cream colored and weighed 3.06 g. A sample of it (150 mg) was converted into Fmoc-EAM-IMR using Fmoc-Cl. Substitution was 0.71 mmole/g (DBU method).

Method E. Reduction with $Ti(O^iPr)_4$—$NaBH_4$ in THF+EtOH (3:1) (2). Four g of IMR-CHO (sub.=1.2 mmole/g, 4.8 mmole/total) was swelled in 40 ml of DMF for approximately 2 hours and then filtered. The resin was washed once with THF and then mixed with 52 ml of THF. Ethylamine (0.8 ml, 12 mmole, 2.5 eq.) and titanium isopropyloxide (3.4 ml, 12 mmole, 2.5 eq.) were added, and the mixture was stirred for 4-5 hours. Eighteen 18 ml of abs. EtOH and 0.7 g of $NaBH_4$ (17.8 mmole, 3.7 eq.) were added, and the mixture was stirred for additional 2-3 hours. The resin was filtered and washed with THF (1 time), 50% THF—$H_2O$ (2 times), DMF (1 time), MeOH (2 times), DCM (2 times), and MeOH (2 times). The resin was dried; it was off-white in color and weighed 5.08 g. A sample of the resin (150 mg) was converted into Fmoc-EAM-IMR using Fmoc-Cl. Substitution was 0.36 mmole/g (DBU method).

Analysis of the properties of the different resins revealed that the reductive amination with $NaBH_4$ (Methods A and B) was the optimal method.

Example 2

Synthesis of Leuprolide Using EAM-IMR Resin

EAM-IMR resin (22.0 g, sub.=0.5 mmole/g, 11 mmole or 0.011 mole/total) was agitated with 100 ml of DMF for an hour. The resin was drained and a solution of Fmoc-amino acid (0.0165 mole, 1.5 eq.) and 1-hydroxybenzotriazole (HOBT; 2.53 g, 0.0165 mole, 1.5 eq.) in 100 ml of DMF+DCM (3:1) was added, and the mixture was agitated. Diisopropylcarbodiimide (DIC; 2.6 ml, 0.0165 mole, 1.5 eq.) was added and agitation was continued for several hours. The progress of the coupling reaction was monitored by a ninhydrin test (see Table 1), which detects free amines. When the reaction was complete, the resin was filtered and washed with DMF (1 time), isopropanol (IPA; 2 times), and DCM (1 time) according to the synthesis protocol (see Table 2). The ninhydrin test was performed again to confirm that the coupling was complete. In case of incomplete coupling, it was either coupled again using 1 mole equivalent of Fmoc-amino acid, HOBT and DIC in DMF+DCM (3:1) as described above or it was acetylated using 5 mole equivalents of acetic anhydride and pyridine based on the result of the ninhydrin test.

TABLE 1

Ninhydrin Test.*

Reagents needed:

0.5 g ninhydrin in 10 ml ethanol
40.0 g phenol in 10 ml ethanol
2 ml 0.001 M KCN in 10 ml pyridine
Method:

1. Place a 3-5 mg sample of the resin in a culture tube and add 3 drops of each reagent (ninhydrin reagent, phenol reagent, KCN reagent).
2. Place culture tube (with resin and reagents) in a heat source (100-110° C.) for 2-5 minutes and observe the color.
Result:

A positive test for amino acids (free amine group) is indicated by a blue-green to blue color.
A negative test for free amino group is indicated by an amber color.

*E. Kaiser, Analytical Biochemistry, 34, 595-598, 1970,

All the amino acids in the sequence were coupled following the synthesis protocol, presented in Table 2. After coupling, the N-α-Fmoc group was removed with 20% piperidine in DMF and the last filtrate was tested with the chloranil test (Table 3).

TABLE 2

First Peptide Synthesis Protocol.

| Step No. | Reagents/Solvents* | Times × Minutes |
|---|---|---|
| 1 | DMF Wash | 1 × 3 minutes |
| 2 | 20% Piperidine in DMF | 2 × 20 minutes |
| 3 | DMF Wash | 5-8 times (until chloranil test is negative) |
| 4 | Coupling in DMF + DCM (3:1) | 4 hours to overnight |
| 5 | DMF wash | 1 × 3 minutes |
| 6 | IPA wash | 2 × 3 minutes |

*6-8 ml/g of resin.

TABLE 3

Chloranil Test.*

Place an aliquot of the wash (3-5 drops) in a culture tube, add approx. 1-2 ml of acetone and 1-2 drops of chloranil reagent (a saturated solution of chloranil in toluene). Shake (or swirl) it for a few seconds. If the color turns blue (dark to light) then piperidine is present. If the color is unchanged or light pale yellow then piperidine is not present and washing is complete.

*T. Christensen, Acta Chemical Scandinavia B, 33, 763-766, 1979.

After the last amino acid (pyro glutamic acid) was coupled and the resin was washed, the peptide-resin was removed from the reactor using IPA, filtered, and dried to yield the pre-Leuprolide resin. The yield was 38.88 g (92.7%) compared to a theoretical yield of 41.95 g. The net gain in weight was 16.88 g (84.6%), compared to a theoretical yield of 19.95 g.

Two g (0.5 mmole) of the peptide-resin was cleaved with 10 ml of TFA+$H_2O$+triisopropylsilane (TIS) (95+2.5+2.5)+1% ethanedithiol (EDT) for 3 hours to yield 0.48 g (78.7%) of the crude Leuprolide. Purity by analytical HPLC was about 64.3% to 69.3% (TFA method—see Table 4) and about 71.3% to 76.3% (TEAP method—see Table 5). According to the HPLC analyses, the purity by weight (yield) was about 83.3% to 72.7% (TFA method) and about 64.8% to 64.0% (TEAP method). Co-injection of the newly synthesized peptide with a reference sample confirmed the presence of the desired peptide—they were identical and inseparable.

To compare the quality of the Leuprolide synthesized on both resins, i.e., EAM-IMR vs. EAM-IA-AMR, a sample of crude Leuprolide synthesized on the previous resin was also analyzed by analytical HPLC at the same time and under the identical HPLC conditions. Its purity was about 69.53% and the purity by weight (yield) was about 83.6% (TFA method). This observation showed that the Leuprolide obtained from both resins were essentially identical in quality and quantity as judged by an analytical HPLC and, therefore, both solid supports are suitable for the synthesis of Leuprolide by the Fmoc-method. The new support, EAM-IMR, is preferable because its synthesis involves only two steps.

TABLE 4

Trifluoroacetic Acid System (TFA) Analytical HPLC Method.

| | |
|---|---|
| Instrument: | Shimadzu |
| Column Type: | Vydac $C_{18}$, 300 Å, 5 μm |
| Column size: | 4.6 × 250 mm |
| Detection wavelength: | 215 nm |
| Flow rate: | 1.0 mL/1 min. |
| Injection volumes: | 20 μL |
| Mobile Phase A: | 0.1% TFA in $H_2O$ |
| Mobile Phase B: | 0.1% TFA in ACN |
| Retention Time: | 15-19 minutes |

TABLE 4-continued

Trifluoroacetic Acid System (TFA) Analytical HPLC Method.

| | |
|---|---|
| Gradients: | 80% A - 20% B/0 minutes |
| | 40% A - 60% B/40 minutes |
| | 80% A - 20% B/40 minutes |
| | 80% A - 20% B/50 minutes |

TABLE 5

Ammonium Phosphate System (TEAP) Analytical HPLC Method.

| | |
|---|---|
| Instrument: | Shimadzu |
| Column type: | Water symmetry $C_{18}$, 100 Å, 5 μm |
| Column size: | 4.6 × 250 mm |
| Detection wavelength: | 215 nm |
| Flow rate: | 1.0 mL/min |
| Injection Volumes: | 10-20 μL of a 1-2 mg/ml of leuprolide solution |
| Mobile Phase: | Solvent A: |
| | 90% 0.087 M Ammonium Phosphate |
| | Monobasic pH 6.0 |
| | 10% ACN |
| | Solvent B: |
| | 40% 0.087 M Ammonium Phosphate |
| | Monobasic pH 6.0 |
| | 60% ACN |
| Gradients: | 30-40% B/25 minutes |
| | 40-100% B/10 minutes |
| | 100% B/0.01 minutes |
| | 30% B/10 minutes |

Example 3

Synthesis of Buserelin Using EAM-IMR Resin

The peptide Buserelin was synthesized on EAM-IMR resin (5.0 g, sub.=0.63 mmole/g, 3.15 mmole/total) using the DIC/HOBT coupling method essentially as described above in Example 2, except that two mole eq. of each amino acid, DIC, and four mole eq. of HOBT were used. The amino acids were: Fmoc-Pro, Fmoc-Arg, Fmoc-Leu, Fmoc-D-Ser (tBu), Fmoc-Tyr (2-Cl-Trt), Fmoc-Ser (Trt), Fmoc-Trp, Fmoc-His (Trt), and pyroGlu. The synthesis protocol is presented in Table 6. The coupling was monitored using the ninhydrin test (Table 1). If coupling was incomplete, it was repeated using the HBTU (i.e., O-(1H-benzotriazole-1-yl)-N,N,N',N'-tetramethyluronium hexafluorophosphate)/HOBT/DIEA method (i.e., 1 eq. amino acid was mixed with 2 eq. HOBT at 0° C., 2 eq. DIEA was added and stirred for about 5 min, 1 eq. HBTU was added and stirred for about 20 min, and coupling to the resin was performed overnight) or acetylated as described above.

TABLE 6

Second Peptide Synthesis Protocol.

| Step No. | Reagents/Solvents | Times × Minutes |
|---|---|---|
| 1 | DMF Wash | 1 × 3 minutes |
| 2 | 20% Piperidine in DMF | 2 × 20 minutes |
| 3 | DMF Wash | 2 × 3 minutes |
| 4 | IPA wash | 1 × 3 minutes |
| 5 | DMF Wash | 3 × 3 minutes (until chloranil test is negative) |
| 6 | Coupling in DMF + DCM (3:1) | 4 hours to overnight |
| 7 | DMF wash | 1 × 3 minutes |
| 8 | IPA wash | 1 × 3 minutes |
| 9 | DMF wash | 1 × 3 minutes |

After the last amino acid (pGlu) was coupled and the resin was washed, the peptide-resin was removed from the reactor using IPA, filtered, and dried. The yield was 11.7 g (104.3%) compared to a theoretical yield of 11.22 g.

Aliquots of the peptide-resin were mixed with various concentrations of TFA/DCM/TIS to deprotect and cleave Buserelin from the resin. The released peptide was captured by filtration, evaporated to dryness, precipitated with ether, dried, and weighed; the purity was analyzed by HPLC.

Sample 1: 2.0 g of peptide-resin was cleaved with 20 ml of 3% TFA/DCM/3% TIS for 1.5 hr—the solid weight of peptide was 0.14 g (20.14%) and purity was about 22.7%. The resin was recleaved with 20 ml of 8% TFA/DCM/5% TIS for 1.5 hr—the solid weight of the peptide was 0.08 g (11.5%) and purity was about 22.2%. The resin was then recleaved with 20 ml of 15% TFA/DCM/5% TIS for 1.5 hr—the solid weight of the released peptide was 0.05 g (7.2%) and purity was about 19.2%. Total yield of the released peptide was 0.27 g (38.8%).

Sample 2: 2.0 g of peptide-resin was cleaved with 20 ml of 2.5% TFA/DCM/5% TIS for 1 hr—the solid weight of the peptide was 0.17 g and purity was about 11.7%. The resin was recleaved with 5% TFA/DCM/5% TIS for 1.5 hr—the solid weight of the released peptide was 0.04 g and purity was about 5.2%. Total yield of the released peptide was 0.21 g.

Sample 3: 1.0 g of peptide-resin was cleaved with 10 ml of 1% TFA/DCM/3% TIS for 1 hr. The solid weight of the peptide was 0.01 g.

Sample 4: 1.0 g of peptide-resin was cleaved with 10 ml of 2% TFA/DCM/3% TIS for 1 hr. The solid weight of the released peptide was 0.06 g.

Sample 5: 5.0 g of peptide-resin was cleaved with 50 ml of 8% TFA/DCM/5% TIS for 1.5 hr. The solid weight of the released peptide was 0.55 g (31.43%) and purity was about 31.93%. The resin was recleaved with 50 ml of 15% TFA/DCM/5% TIS for 1.5 hr. The solid weight of the released peptide was 0.32 g (18.3%) and purity was about 23%. The total weight of the released peptide was 0.87 g (49.7%).

Example 4

Synthesis of Deslorelin Using EAM-IMR Resin

The peptide Deslorelin was synthesized on EAM-IMR resin (10.0 g, sub.=0.6 mmole/g, 6 mmol/total) using the DIC/HOBT coupling method essentially as described above in Example 2, except that two mole eq. of each amino acid and reagent were used. The amino acids were: Fmoc-Pro, Fmoc-Arg (Pbf), Fmoc-Leu, Fmoc-D-Trp (Boc), Fmoc-Tyr (tBu), Fmoc-Ser (tBu), Fmoc-Trp (Boc), Fmoc-His (Trt), and pyro-Glu. The synthesis protocol is presented in Tables 2 and 6. The coupling was monitor54ed using the ninhydrin test (Table 1).

After completion of the synthesis, the washed resin was dried to yield peptide-resin in 100% yield.

Two g (0.54 mmole) of the peptide-resin was cleaved with 10 ml of TFA+$H_2O$+TIS+dithioerythritol (DTE) (92.5+2.5+2.5+2.5) for 3 hr to yield 0.7 g (100%) of the crude peptide. Purity by analytical HPLC was about 84.2% (TFA method) and yield by weight was 66.95%.

Two g (0.54 mmole) of the peptide-resin was cleaved with 10 ml of TFA+$H_2O$+phenol+thioanisole+DTE (82.5+5+5+5+2.5) for 3 hr to yield 0.67 g (95.7%) of the crude peptide. Purity by analytical HPLC was about 68.3% (TFA method).

Example 5

Synthesis of Alarelin Using EAM-IMR Resin

The peptide Alarelin was synthesized on EAM-IMR resin (8.5 g, sub.=0.6 mmole/g, 5 mmol/total) using the DIC/HOBT coupling method essentially as described above in Example 2. The amino acids were: Fmoc-Pro, Fmoc-Arg (Pbf), Fmoc-Leu, Fmoc-D-Ala, Fmoc-Tyr (tBu), Fmoc-Ser (tBu), Fmoc-Trp (Boc), Fmoc-His (Trt), and pyroGlu. The synthesis protocol is presented in Tables 2 and 6. The coupling was monitored using the ninhydrin test (Table 1).

After completion of the synthesis, the peptide-resin was washed and dried to yield 18.5 g (102%) of the peptide-resin compared to a theoretical yield of 18.1 g.

One g (0.28 mmole) of the peptide-resin was cleaved with 10 ml of TFA+$H_2O$+TIS+DTE (92.5+2.5+2.5+2.5) for 3 hr to yield 0.31 g (94.2%) of the crude peptide. Yield by weight was about 81.4% and purity by analytical HPLC was about 81.4% (TFA method).

What is claimed is:

1. A compound comprising Formula (I):

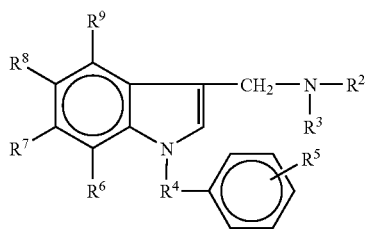

(I)

wherein:
$R^2$ and $R^4$ are hydrocarbyl;
$R^3$ is selected from the group consisting of hydrogen, a protecting group, an amino acid residue, and a peptide;
$R^5$ is a solid support comprising at least one polymer; and
$R^6$, $R^7$, $R^8$, and $R^9$ are independently selected from the group consisting of hydrogen, hydrocarbyl, and substituted hydrocarbyl.

2. The compound of claim 1, wherein $R^3$ is selected from the group consisting of Fmoc and a peptide; and $R^5$ is polystyrene cross-linked with divinylbenzene.

3. The compound of claim 2, wherein the peptide has a C-terminus secondary amine.

4. The compound of claim 1, comprising:

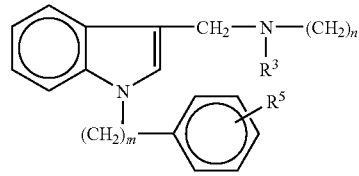

wherein:
$R^3$ is selected from the group consisting of hydrogen, a protecting group, an amino acid residue, and a peptide;
$R^5$ is a solid support comprising at least one polymer;
m is an integer from 1 to 8; and
n is an integer from 1 to 8.

5. The compound of claim 4, wherein $R^3$ is selected from the group consisting of Fmoc and a peptide; and $R^5$ is polystyrene cross-linked with divinylbenzene.

6. The compound of claim 5, wherein the peptide has a C-terminus secondary amine.

7. The compound of claim 1, comprising:

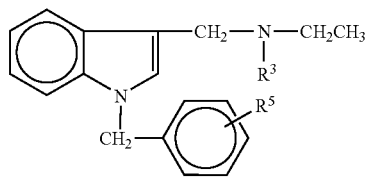

wherein:
R³ is selected from the group consisting of hydrogen, a protecting group, an amino acid residue, and a peptide; and
R⁵ is a solid support comprising at least one polymer.

8. The compound of claim 7, wherein R³ is selected from the group consisting of Fmoc and a peptide; and R⁵ is polystyrene cross-linked with divinylbenzene.

9. The compound of claim 8, wherein the peptide has a C-terminus secondary amine.

10. The compound of claim 8, wherein the peptide is selected from the group consisting of Leuprolide, Deslorelin, Buserelin, Alarelin, Fertirelin, and Histrelin.

11. A process for making a solid support, the process comprising:
(a) combining a compound comprising formula (1) with a compound comprising formula (2) in the presence of a base to produce a compound comprising formula (3), wherein the compound comprising formula (1) has the following structure:

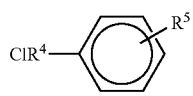

wherein:
R⁴ is hydrocarbyl; and
R⁵ is a solid support comprising at least one polymer;
the compound comprising formula (2) has the following structure:

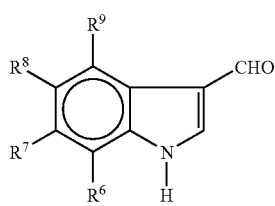

wherein:
R⁶, R⁷, R⁸, and R⁹ are independently selected from the group consisting of hydrogen, hydrocarbyl, and substituted hydrocarbyl; and
the compound comprising formula (3) has the following structure:

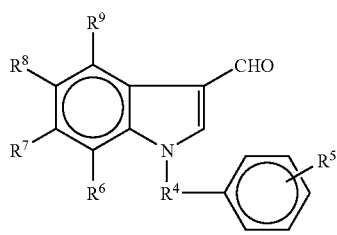

wherein:
R⁴ is hydrocarbyl;
R⁵ is a solid support comprising at least one polymer; and
R⁶, R⁷, R⁸, and R⁹ are independently selected from the group consisting of hydrogen, hydrocarbyl, and substituted hydrocarbyl;
(b) contacting the compound comprising formula (3) with a reducing agent and a compound comprising R²NH₂,
wherein R² is hydrocarbyl, to produce a solid support comprising formula (I);

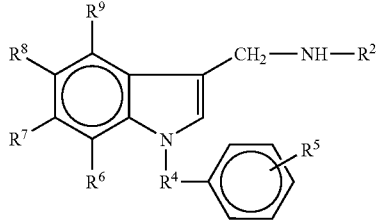

wherein:
R² and R⁴ are hydrocarbyl;
R⁵ is a solid support comprising at least one polymer; and
R⁶, R⁷, R⁸, and R⁹ are independently selected from the group consisting of hydrogen, hydrocarbyl, and substituted hydrocarbyl.

12. The process of claim 11, wherein the base is selected from the group consisting of sodium methoxide, potassium carbonate, lithium carbonate, sodium carbonate, magnesium carbonate, calcium carbonate, and strontium carbonate; and the amount of compound 1 to the amount of compound 2 to the amount of base is a molar ratio ranging from about 1:1:1 to about 1:5:5.

13. The process of claim 11, wherein the reducing agent is selected from the group consisting of sodium borohydride, sodium cyanoborohydride, diisobutylaluminium hydride, lithium aluminium hydride, and titanium isopropoxide sodium borohydride; and the amount of compound 3 to the amount of R²NH₂ to the amount of reducing agent is a molar ratio ranging from about 1:1:1 to about 1:10:20.

14. The process of claim 11, wherein the base is potassium carbonate; the reducing agent is sodium borohydride; the amount of compound 1 to the amount of compound 2 to the amount of potassium carbonate is a molar ratio ranging from about 1:1:1 to about 1:5:5; and the amount of compound 3 to the amount of R²NH₂ to the amount of sodium borohydride is a molar ratio ranging from about 1:1:1 to about 1:10:20.

15. The process of claim 11, wherein:
the compound comprising formula (1) has the following structure:

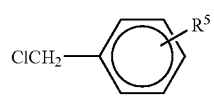

the compound comprising formula (2) has the following structure:

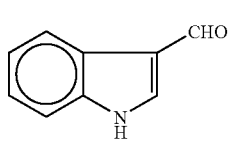

the compound comprising formula (3) has the following structure:

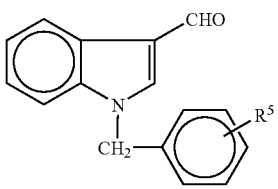

and the compound comprising formula (I) has the following structure:

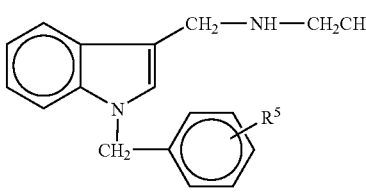

wherein $R^5$ is solid support comprising at least one polymer.

16. The process of claim 15, wherein $R^5$ is polystyrene cross-linked with divinylbenzene; the base is potassium carbonate; the $R^2NH_2$ is ethylamine; the reducing agent is sodium borohydride; the amount of compound 1 to the amount of compound 2 to the amount about of potassium carbonate is a molar ratio ranging from about 1:1:1 to about 1:5:5; and the amount of compound 3 to the amount of ethylamine to the amount of sodium borohydride is a molar ratio ranging from about 1:1:1 to about 1:10:20.

17. A method for synthesizing a polypeptide, the method comprising:
(a) activating the carboxyl group of an amino acid that has its amine protected by a Fmoc group, and its side chain protected by an acid labile group;
(b) coupling the activated amino acid to the amino group of a solid support comprising Formula (I):

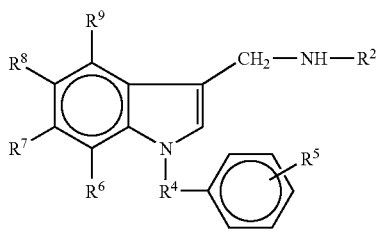

wherein:
$R^2$ and $R^4$ are hydrocarbyl;
$R^5$ is a solid support comprising at least one polymer; and
$R^6$, $R^7$, $R^8$, and $R^9$ are independently selected from the group consisting of hydrogen, hydrocarbyl, and substituted hydrocarbyl;
(c) treatment of the solid support with a base to deprotect the amine group of the amino acid protected with Fmoc; and
(d) repeating steps (a) to (c) until the target polypeptide is synthesized.

18. The method of claim 17, wherein the polypeptide is selected from the group consisting of Leuprolide, Deslorelin, Buserelin, Alarelin, Fertirelin, and Histrelin.

19. The method of claim 17, further comprising cleaving the target polypeptide from the solid support by contacting the solid support of step (d) with a weak acid and a scavenger selected from the group consisting of phenol, water, 1,2-ethanedithiol, and triisopropylsilane.

20. The method of claim 17, wherein the solid support has the following structure:

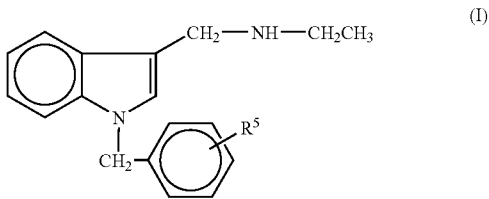

wherein $R^5$ is polystyrene cross-linked with divinylbenzene.

* * * * *

```
                        SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa = pyroglutamic acid
<220> FEATURE:
<221> NAME/KEY: misc_feature
<222> LOCATION: (6)..(6)
<223> OTHER INFORMATION: Xaa = D-leucine
<220> FEATURE:
<221> NAME/KEY: misc_feature
<222> LOCATION: (9)..(9)
<223> OTHER INFORMATION: Xaa = proline with carboxy terminus ethylamide

<400> SEQUENCE: 1

Xaa His Trp Ser Tyr Xaa Leu Arg Xaa
1               5
```